US012690857B1

(12) United States Patent
Chen et al.

(10) Patent No.: US 12,690,857 B1
(45) Date of Patent: Jul. 28, 2026

(54) ANNULAR SURGICAL RETRACTOR

(71) Applicant: National Taiwan University, Taipei City (TW)

(72) Inventors: Cheng-Wei Chen, Taipei City (TW); Shu-Chien Huang, Taipei City (TW); Wei-Qi Liu, Taipei City (TW)

(73) Assignee: NATIONAL TAIWAN UNIVERSITY, Taipei City (TW)

( * ) Notice: Subject to any disclaimer, the term of this patent is extended or adjusted under 35 U.S.C. 154(b) by 0 days.

(21) Appl. No.: 19/247,234

(22) Filed: Jun. 24, 2025

(30) Foreign Application Priority Data

May 16, 2025 (TW) .................................. 114118443

(51) Int. Cl.
　　*A61B 17/02* (2006.01)
　　*A61B 1/05* (2006.01)
(52) U.S. Cl.
　　CPC ............ *A61B 17/0293* (2013.01); *A61B 1/05* (2013.01); *A61B 17/0206* (2013.01)
(58) Field of Classification Search
　　CPC ............ A61B 17/0293; A61B 17/0206; A61B 17/0218
　　See application file for complete search history.

(56) References Cited

U.S. PATENT DOCUMENTS

| 2005/0215863 A1* | 9/2005 | Ravikumar | ........ A61B 17/0293 |
| | | | 600/204 |
| 2011/0237898 A1* | 9/2011 | Stone | ................. A61B 17/0293 |
| | | | 600/205 |
| 2022/0257232 A1* | 8/2022 | Soliman | ............. A61B 17/0206 |

* cited by examiner

*Primary Examiner* — Julianna N Harvey
(74) *Attorney, Agent, or Firm* — MUNCY, GEISSLER, OLDS & LOWE, P.C.

(57) ABSTRACT

An annular surgical retractor has a base panel, a driving panel, and multiple expanding elements. Each of the expanding elements has a transmission panel and a supporting rod formed on an inner end of the transmission panel and is bent relative to the transmission panel. By driving the driving panel to rotate relative to the base panel, each of the expanding elements is driven to move between a retracting position and an expanding position. When in the retracting position, the supporting rods abut on each other to form a column. When moved to the expanding position, distances between the supporting rods are enlarged and an area surrounded by the supporting rods is expanded. The annular surgical retractor is used to open a small incision. A depth of the supporting rods inserted into the incision and the area surrounded by the supporting rods can be adjusted according to surgical needs.

15 Claims, 13 Drawing Sheets

ANNULAR SURGICAL RETRACTOR

BACKGROUND OF THE INVENTION

1. Field of the Invention

The present invention relates to a surgical instrument, especially to an annular surgical retractor used to hold away soft tissue or ribs during surgery.

2. Description of the Prior Art(s)

A surgical retractor is a surgical aid, and is used to separate edges of an incision on the human body during surgery and even to push away soft tissue or ribs that block a surgical site, to facilitate medical personnel to perform surgery.

With reference to FIG. 11, a conventional surgical retractor 50 comprises two arms 51. Each of the arms 51 has a pivotal portion 511, a supporting portion 512, and a handle 513. The pivotal portion 511 is formed on a middle of the arm 51 and is pivotally connected with the pivotally portion 511 of the other arm 51, making the conventional surgical retractor 50 look like a scissors. The supporting portion 512 is formed on a front end of the arm 51 and includes multiple hooking plates 5121. The handle 513 is formed on a rear end of the arm 51 and is held by an operator to drive the two arms 51 to pivot, such that the supporting portions 512 of the two arms 51 move closer or farther away from each other.

With further reference to FIG. 12, when in use, the operator holds the handles 513 of the arms 51 of the conventional surgical retractor 50 with one hand, drives the supporting portions 512 of the two arms 51 to move closer to each other, then inserts the supporting portions 512 into an incision 60 to be opened, and rests the supporting portions 512 against the edges of the incision 60. Then the operator drives the supporting portions 512 of the two arms 51 to move away from each other to expand the incision 60, so as to allow the medical personal to see where surgery is to be performed.

However, the conventional surgical retractor 50 has the following shortcomings. First, in order to allow the hooking plates 5121 arranged on the front ends of the arms 51 to be inserted in to the incision 60, an initial length of the incision 60 needs to be at least 21 millimeter (mm). A wound that is too large would not only cause a physical burden on the patient, but would also prolong the subsequent recovery time. Moreover, as shown in FIG. 12, the supporting portions 512 of the two arms 51 moves in opposite directions when in use, making it impossible to push a front end edge of the incision 60. Consequently, a rod-shaped retractor is needed to hold away the front end edge of the incision 60, such that the incision 60 is able to be opened to a size that allows a clear view of a location where surgery is to be performed. It is inconvenient to open the incision 60 by using the conventional surgical retractor 50. In addition, a maximum depth of the hooking plates 5121 of the supporting portions 512 inserted into the incision 60 is about 11 mm. Therefore, the conventional surgical retractor 50 can only be used to expand the incision 60 of a surface of the human body and is unable to be used to expand tissues located in deeper layers.

To overcome the shortcomings, the present invention provides an annular surgical retractor to mitigate or obviate the aforementioned problems.

SUMMARY OF THE INVENTION

The main objective of the present invention is to provide an annular surgical retractor comprises a base panel, a driving panel, and multiple expanding elements.

The base panel includes a stationary annular plate and a stationary handle. The stationary annular plate has a through hole formed through the stationary annular plate, and multiple guiding portions disposed on an inner side surface of the stationary annular plate and sequentially arranged around the through hole of the stationary annular plate. Each of the guiding portions is elongated and has a retracting end positioned toward an inner annular edge of the stationary annular plate and an expanding end positioned toward an outer annular edge of the stationary annular plate. The retracting end of the guiding portion and the expanding end of the guiding portion are located at different radial extension lines of the stationary annular plate. The stationary handle is securely attached to the outer annular edge of the stationary annular plate.

The driving panel includes a movable annular plate and a movable handle. The movable annular plate has a through hole formed through the movable annular plate, an inner side surface facing toward the inner side surface of the stationary annular plate, and multiple driving portions disposed on the inner side surface of the movable annular plate and arranged around the through hole of the movable annular plate. The movable handle is securely attached to an outer annular edge of the movable annular plate.

The expanding elements are disposed between the base panel and the driving panel and arranged annularly. Each of the expanding elements has a transmission panel and a supporting rod. The transmission panel is disposed between the stationary annular plate and the movable annular plate, and has a first side surface facing toward the stationary annular plate, a second side surface facing toward the movable annular plate, an inner end disposed between the through hole of the stationary annular plate and the through hole of the movable annular plate, an outer end disposed between the stationary annular plate and the movable annular plate, a sliding portion, and a transmission portion. The sliding portion is disposed on the first side surface of the transmission panel. The sliding portions of the transmission panels of the expanding elements are movably mounted with the guiding portions of the stationary annular plates respectively to allow each of the sliding portions to move along a respective one of the guiding portions. The transmission portion is disposed on the second side surface of the transmission panel. The transmission portion has a retracting end positioned toward the outer annular edge of the movable annular and an expanding end positioned toward the inner annular edge of the movable annular plate. The transmission portions of the transmission panels of the expanding elements are movably mounted with the driving portions of the movable annular plate respectively to allow each of the driving portions to move along a respective one of the transmission portions. The supporting rod is formed on the inner end of the transmission panel, is bent relative to the transmission panel, and protrudes outward from the through hole of the stationary annular plate.

The expanding elements are driven by the driving panel to move back and forth between a retracting position and an expanding position.

When each of the expanding elements is located at the retracting position, each of the driving portions of the movable annular plate is located at the retracting end of the transmission portion of a respective one of the expanding elements, the sliding portion of each of the expanding elements is located at the retracting end of a respective one of the guiding portions of the stationary annular plate, and the supporting rods of the expanding elements abut on each other side by side to form a column.

When each of the expanding elements is moved to the expanding position, each of the driving portions of the movable annular plate is moved to the expanding end of the transmission portion of a respective one of the expanding elements, the sliding portion of each of the expanding elements is moved to the expanding end of the respective one the guiding portions of the stationary annular plate, and the supporting rods of the expanding elements are separately arranged annularly.

When using the annular surgical retractor, an incision to be expanded only need to be about 8 millimeter (mm) to allow the supporting rods of the expanding elements to be inserted into the incision. Small incision can reduce a physical burden on the patient and effectively shorten healing time.

Moreover, a depth of the supporting rods inserted into the incision and the area surrounded by the supporting rods can be adjusted according to surgical needs.

In addition, when the supporting rods of the expanding elements move toward the expanding positions, the area for performing surgery surrounded by the supporting rods is annular expanded. That is, the operator is able to push the internal tissues in all directions around at the same time, making the annular surgical retractor highly flexible in use.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
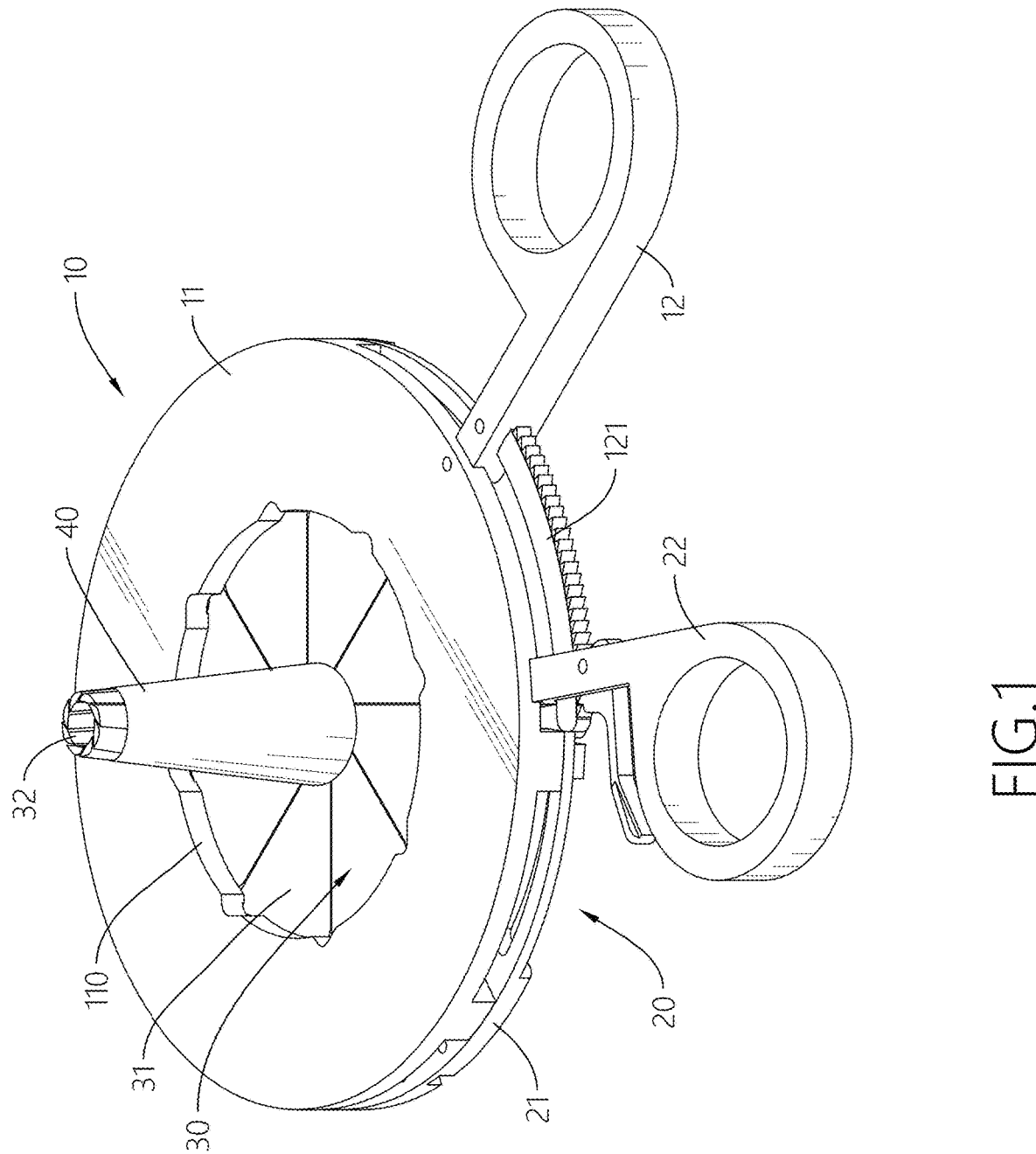
FIG. 1 is a top perspective view of an annular surgical retractor in accordance with the present invention, shown in a retracting state.
Figure 3:
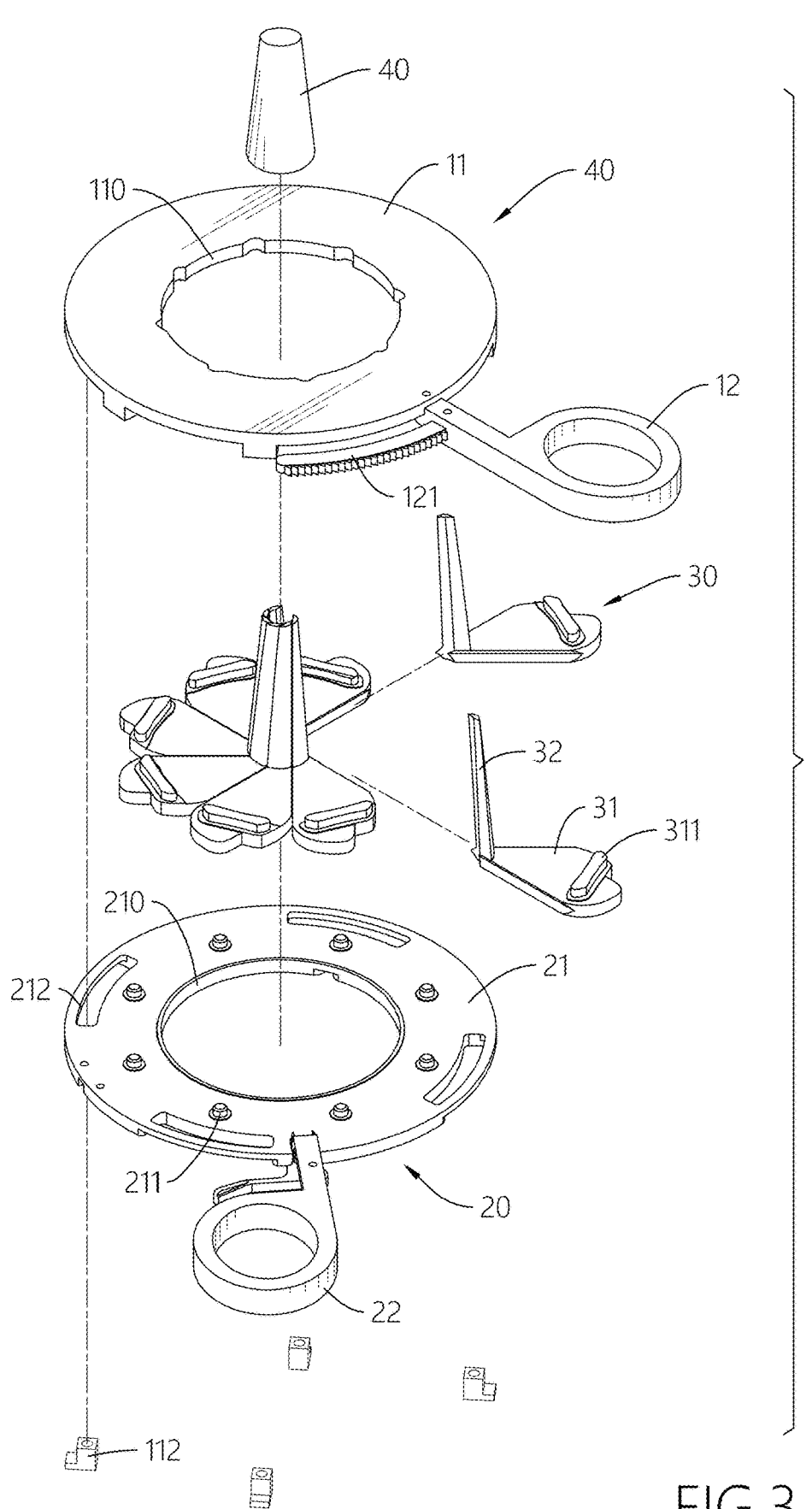
FIG. 3 is an exploded top perspective view of the annular surgical retractor in FIG. 1.

With reference to FIGS. 1 and 3, an annular surgical retractor in accordance with the present invention comprises a base panel 10, a driving panel 20, multiple expanding elements 30, and an elastic sleeve 40.

Figure 4:
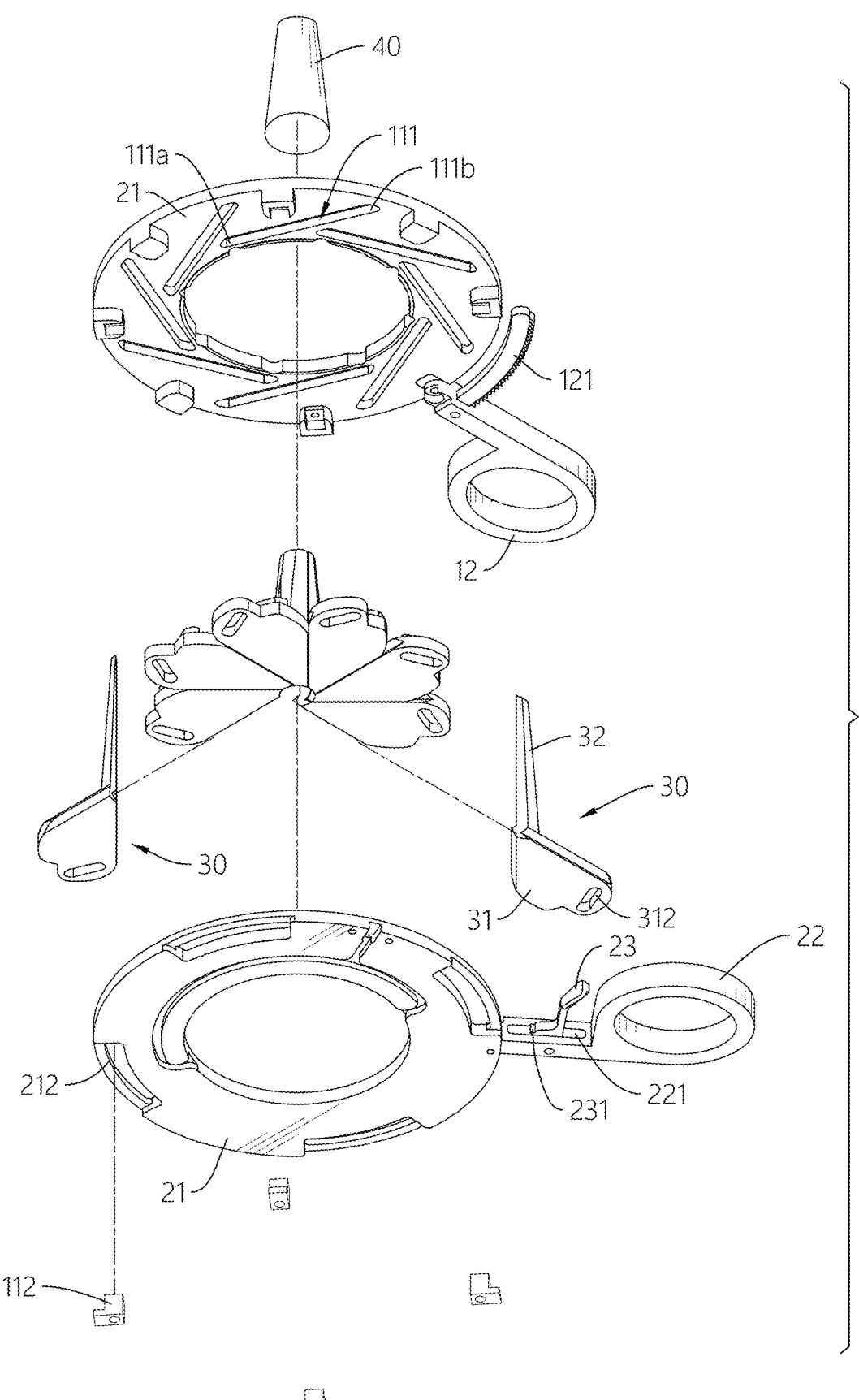
FIG. 4 is an exploded bottom perspective view of the annular surgical retractor in FIG. 1.

With further reference to FIGS. 3 and 4, the base panel 10 includes a stationary annular plate 11 and a stationary handle 12. A through hole 110 is formed through the stationary annular plate 11, such that the stationary annular plate 11 is annular and has an inner annular edge and an outer annular edge. The stationary annular plate 11 further has an inner side surface, multiple guiding portions 111 and multiple limiting protrusions 112.

Figure 5:
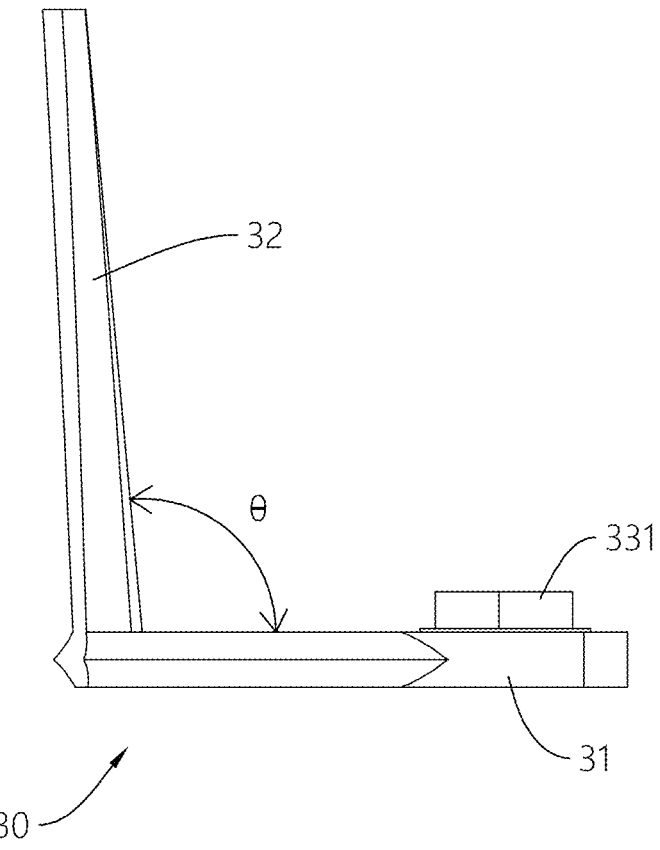
FIG. 5 is a side view of an expanding element of the annular surgical retractor in FIG. 1.
Figure 6:
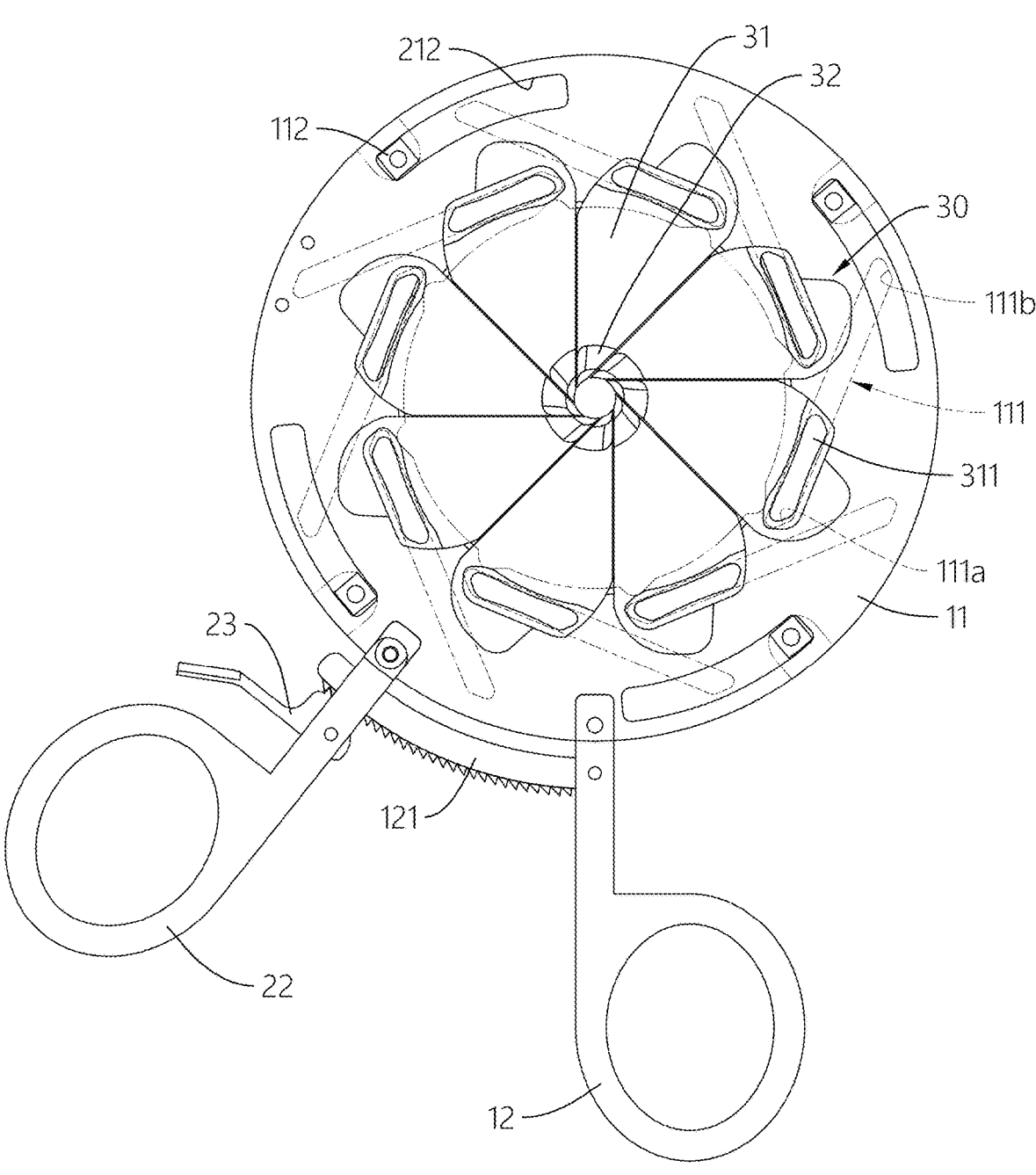
FIG. 6 is a top view of the annular surgical retractor in FIG. 1, shown in the retracting state.

With further reference to FIGS. 4 and 5, the guiding portions 111 are disposed on the inner side surface of the stationary annular plate 11 and are sequentially arranged around the through hole 110 of the stationary annular plate 11. Each of the guiding portions 111 is elongated and has a retracting end 111a and an expanding end 111b. The retracting end 111a of the guiding portion 111 is positioned toward the inner annular edge of the stationary annular plate 11. The expanding end 111b of the guiding portion 111 is positioned toward the outer annular edge of the stationary annular plate 11. The retracting end 111a of the guiding portion 111 and the expanding end 111b of the guiding portion 111 are located at different radial extension lines of the stationary annular plate 11, such that each of the guiding portions 111 extends nonparallel to any one of the radial extension lines of the stationary annular plate 11. The limiting protrusions 112 are disposed on the inner side surface of the stationary annular plate 11 and are separately arranged along the outer annular edge of the stationary annular plate 11. In the preferred embodiment, the limiting protrusions 112 are detachably mounted on the inner side surface of the stationary annular plate 11.

The stationary handle 12 is securely attached to the outer annular edge of the stationary annular plate 11.

With further reference to FIGS. 3 and 5, the driving panel 20 includes a movable annular plate 21 and a movable handle 22.

A through hole 210 is formed through the movable annular plate 21, such that the movable annular plate 21 is annular and has an inner annular edge and an outer annular edge. The movable annular plate 21 further has an inner side surface, multiple driving portions 211 and multiple limiting guide slots 212. The inner side surface of the movable annular plate 21 faces toward the inner side surface of the stationary annular plate 11. The driving portions 211 are disposed on the inner side surface of the movable annular plate 21 and are arranged around the through hole 210 of the movable annular plate 21. The limiting guide slots 212 are separately arranged along the outer annular edge of the movable annular plate 21. Each of the limiting guide slots 212 is formed as an arc-shaped elongated hole and extends along the outer annular edge of the movable annular plate 21. The limiting protrusions 112 of the stationary annular plate 11 slidably protrude in the limiting slots 212 respectively, such that the movable annular plate 21 is limited to rotate relative to the stationary annular plate 11 in a limited angle.

The movable handle 22 is securely attached to the outer annular edge of the movable annular plate 21. An operator holds the stationary handle 12 of the base panel 10 and the movable handle 22 of the driving panel 20 with one hand and drives the movable annular plate 21 to rotate relative to the stationary annular plate 11 with his thumb.

The expanding elements 30 are disposed between the base panel 10 and the driving panel 20 and are arranged annularly. The expanding elements 30 are able to be driven by the driving panel 20 to move back and forth between a retracting position and an expanding position. Each of the expanding elements 30 has a transmission panel 31 and a supporting rod 32.

The transmission panel 31 is disposed between the stationary annular plate 11 and the movable annular plate 21, and has a first side surface, a second side surface, an inner end, an outer end, a sliding portion 311 and a transmission portion 312. The first side surface faces toward the stationary annular plate 11. The second side surface faces toward the movable annular plate 21. The inner end is disposed between the through hole 110 of the stationary annular plate 11 and the through hole 210 of the movable annular plate 21. The outer end is disposed between the stationary annular plate 11 and the movable annular plate 21. In the preferred embodiment, the transmission panel 31 is drop-shaped, such that the inner end is formed as a tip and the outer end is formed as a blunt end.

The sliding portion 311 is disposed on the first side surface of the transmission panel 31 and is located on the outer end of the transmission panel 31. The sliding portions 311 of the transmission panels 31 of the expanding elements 30 are movably mounted with the guiding portions 111 of the stationary annular plates 11 respectively to allow each of the sliding portions 311 to move along a respective one of the guiding portions 111. In the preferred embodiment, the guiding portion 111 is formed as an elongated guiding groove; and the sliding portion 311 is formed as a protrusion and is mounted in the respective one of the guiding portions 111, which is formed as said elongated guiding groove, so as to move along the guiding portion 111. Preferably, the sliding portion 311 is formed into an elongated protrusion with a length shorter than the guiding portion 111. However, the structure of the guiding portion 111 and the sliding portion 311 is not limited thereto, as long as the sliding portion is able to move along the respective one of the guiding portions 111.

The transmission portion 312 is disposed on the second side surface of the transmission panel 31 and is located on the outer end of the transmission panel 31. The transmission portion 312 has a retracting end 312a and an expanding end 312b. The retracting end 312a of the transmission portion 312 is positioned toward the outer annular edge of the movable annular plate 21. The expanding end 312b of the transmission portion 312 is positioned toward the inner annular edge of the movable annular plate 21. The transmission portions 312 of the transmission panels 31 of the expanding elements 30 are movably mounted with the driving portions 211 of the movable annular plate 21 respectively to allow each of the driving portions 211 to move along a respective one of the transmission portions 312. In the preferred embodiment, the transmission portion 312 is formed as an elongated guiding groove; and the driving portion 211 is formed as a protrusion and is mounted in the respective one of the transmission portions 312, which is formed as said elongated guiding groove, so as to move along the transmission portion 312. However, the structure of the transmission portion 312 and the driving portion 211 is not limited thereto, as long as the driving portion 211 is able to move along the respective one of the transmission portions 312.

With further reference to FIGS. 1, 3 and 5, the supporting rod 32 is formed on the inner end of the transmission panel 31, is bent relative to the transmission panel 31, and protrudes outward from the through hole 110 of the stationary annular plate 11. The elastic sleeve 40 is mounted around the supporting rods 32 of the expanding elements 30.

Figure 10:
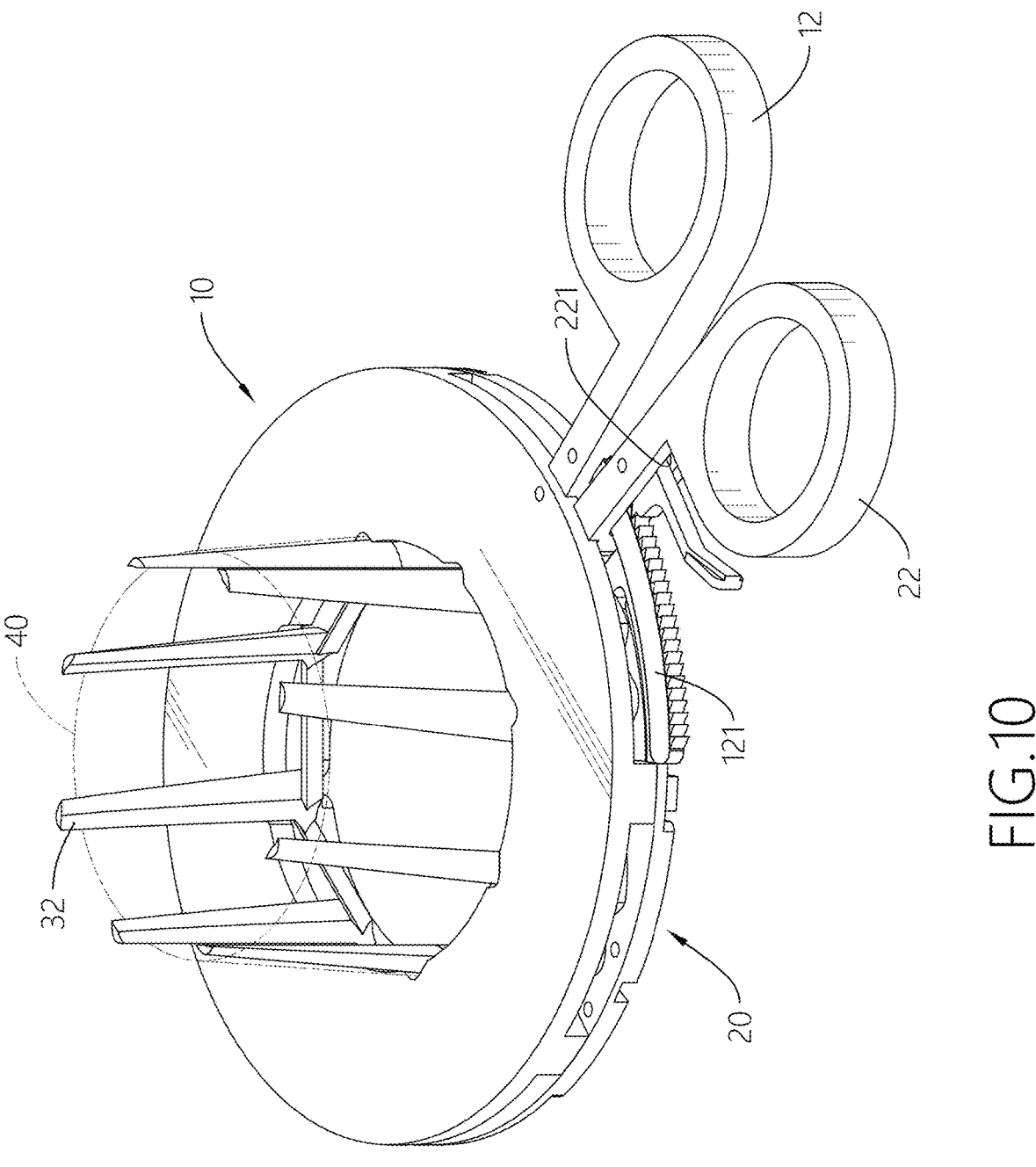
FIG. 10 is a top perspective view of the annular surgical retractor in FIG. 1, shown in the expanding state.

As shown in FIG. 1, when each of the expanding elements 30 is located at the retracting position, the supporting rods 32 of the expanding elements 30 abut on each other side by side to form a column. With further reference to FIG. 10, when each of the expanding elements 30 is moved to the expanding position, the supporting rods 32 of the expanding elements 30 are separately arranged annularly. In the preferred embodiment, an included angle θ between the supporting rod 32 and the transmission panel 31 is slightly larger than 90 degrees. Thus, each of the expanding elements 30 is located at the retracting position, the supporting rods 32 of the expanding elements 30 form a conical column that tapers away from the transmission panels 31 of the expanding elements 30 to facilitate insertion of the supporting rods 32 into an incision to be opened on the human body. Specifically, said included angle θ is defined between 90 degrees to 100 degrees. In embodiment shown in the drawings, the included angle θ is 95.8 degrees.

With reference to FIGS. 1, 2, 6 and 8, when each of the expanding elements 30 is located on the retracting position and the annular surgical retractor is in a retracting state, each of the driving portions 211 of the movable annular plate 21 is located at the retracting end 312a of the transmission portion 312 of a respective one of the expanding elements 30 and the sliding portion of each of the expanding elements 30 is located at the retracting end 111a of a respective one of the guiding portions 111 of the stationary annular plate 11. Meanwhile, the inner ends of the transmission panels 31 of the expanding elements 30 abut on each other and the supporting rods 32 abut on each other side by side. The operator holding the annular surgical retractor is able to insert the column-shaped supporting rods 32 into the incision to be opened on the human body.

Figure 7:
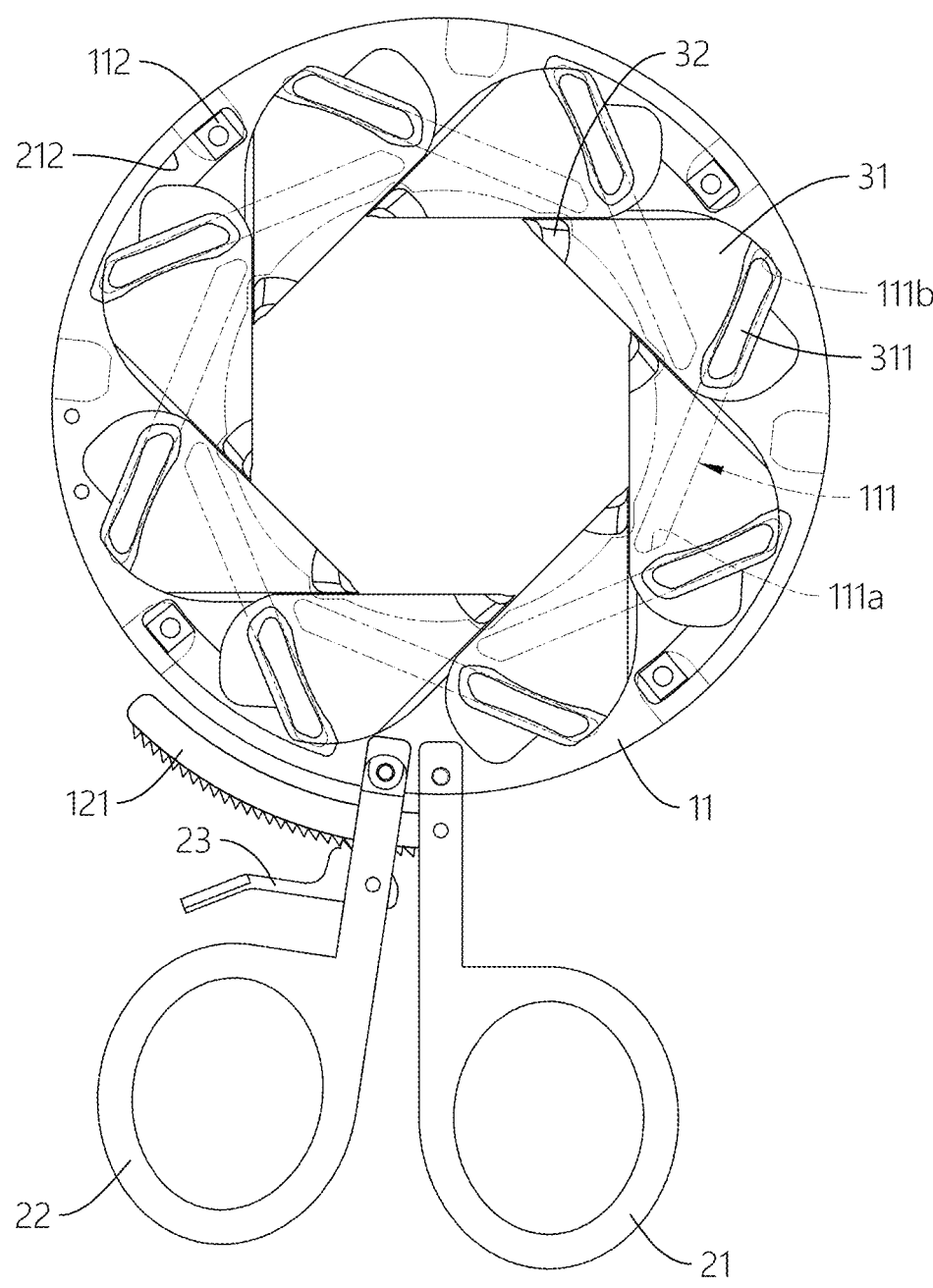
FIG. 7 is a top view of the annular surgical retractor in FIG. 1, shown in an expanding state.
Figure 8:
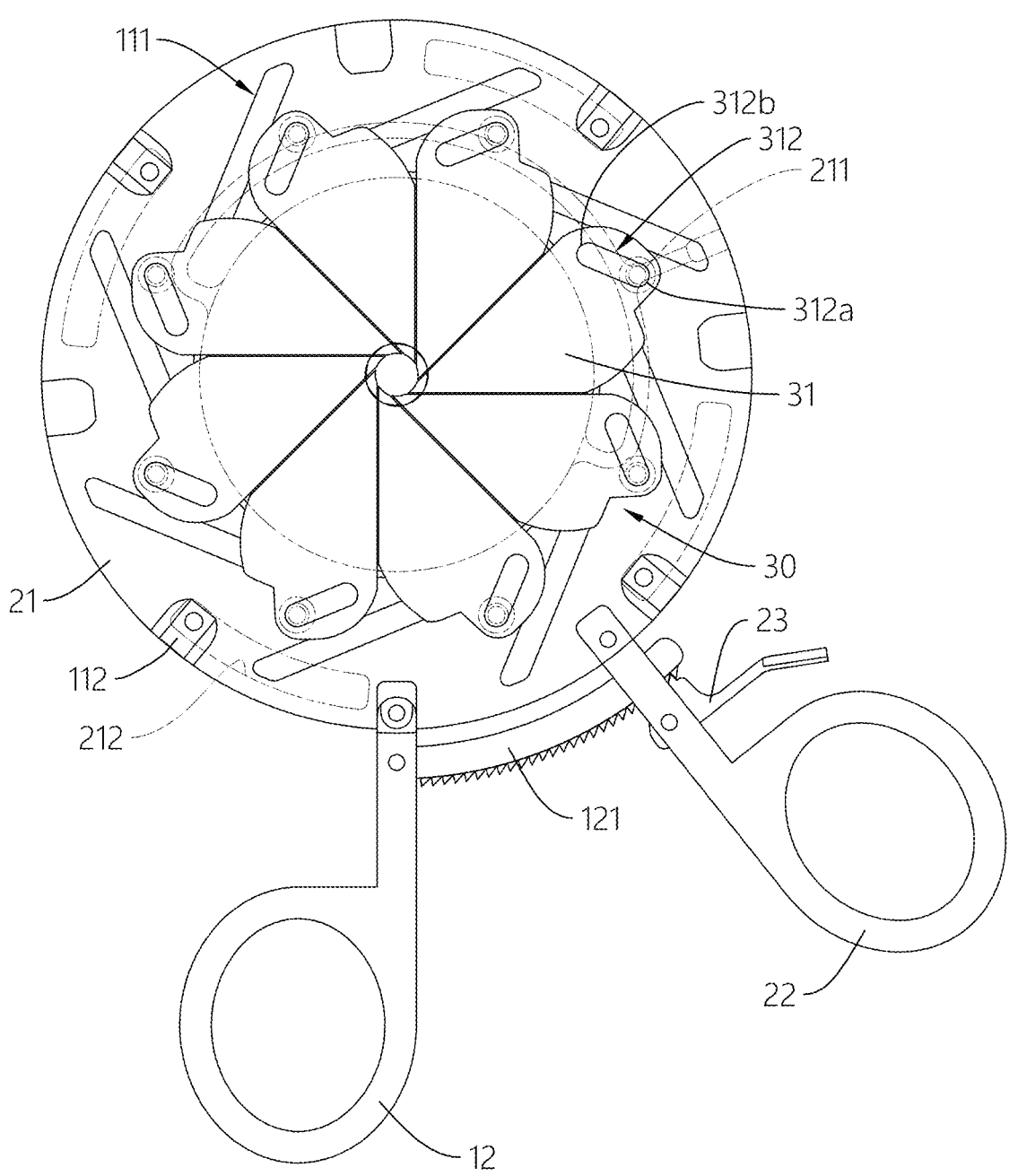
FIG. 8 is a bottom view of the annular surgical retractor in FIG. 1, shown in the retracting state.
Figure 9:
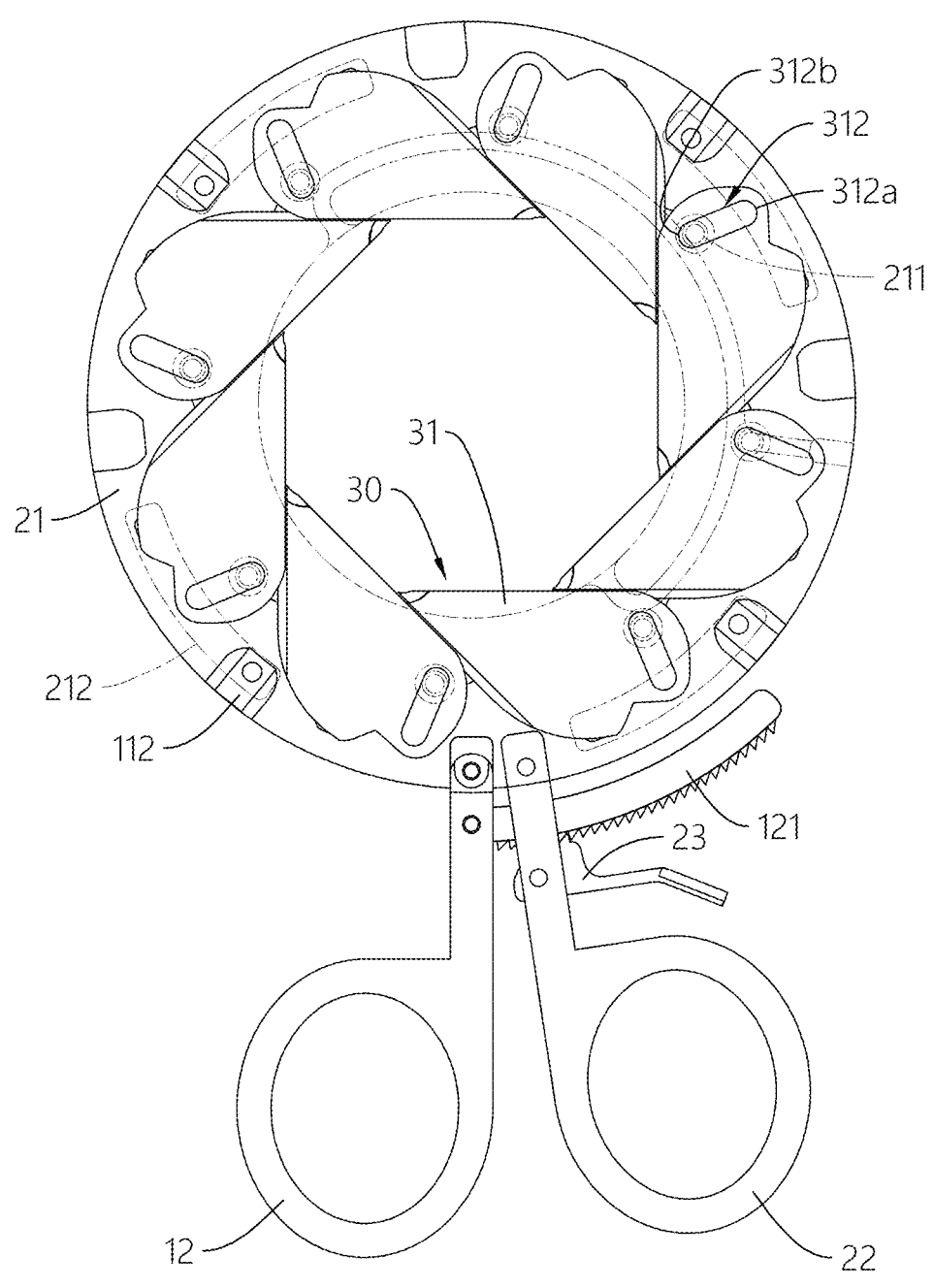
FIG. 9 is a bottom view of the annular surgical retractor in FIG. 1, shown in the expanding state.

With reference to FIGS. 7, 9 and 10, when the operator drives the movable annular plate 21 to rotate relative to the stationary annular plate 11 through the movable handle 22 of the driving panel 20 to drive each of the expanding elements 30 to move to the expanding position and the annular surgical retractor is in an expanding state, each of the driving portions 211 of the movable annular plate 21 moves toward the expanding end 312b of the transmission portion 312 of a respective one of the expanding elements 30, so as to drive the sliding portion 311 of each of the expanding elements 30 to move toward the expanding end 111b of the respective one the guiding portions 111 of the stationary annular plate 11. Meanwhile, the inner end of the transmission panel 31 of each of the expanding elements 30 moves along a side edge of the transmission panel 31 of an adjacent one of the expanding elements toward the outer end of the transmission panel 31 of said adjacent one of the expanding elements 30, to enlarged distances between the supporting rods 32 of the expanding elements 30. Accordingly, the elastic sleeve 40 is expanded, an area surrounded by the supporting rods 32 of the expanding elements 30 is enlarged, and the incision is also expanded.

An angle of rotation of the movable annular plate 21 relative to the stationary annular plate 11 is able to be adjusted according to actual surgical needs such as sizes of the incisions, ranges of wounds and so on. Thus, the area surrounded by the supporting rods 32 of the expanding elements 30 can be controlled.

Figure 11:
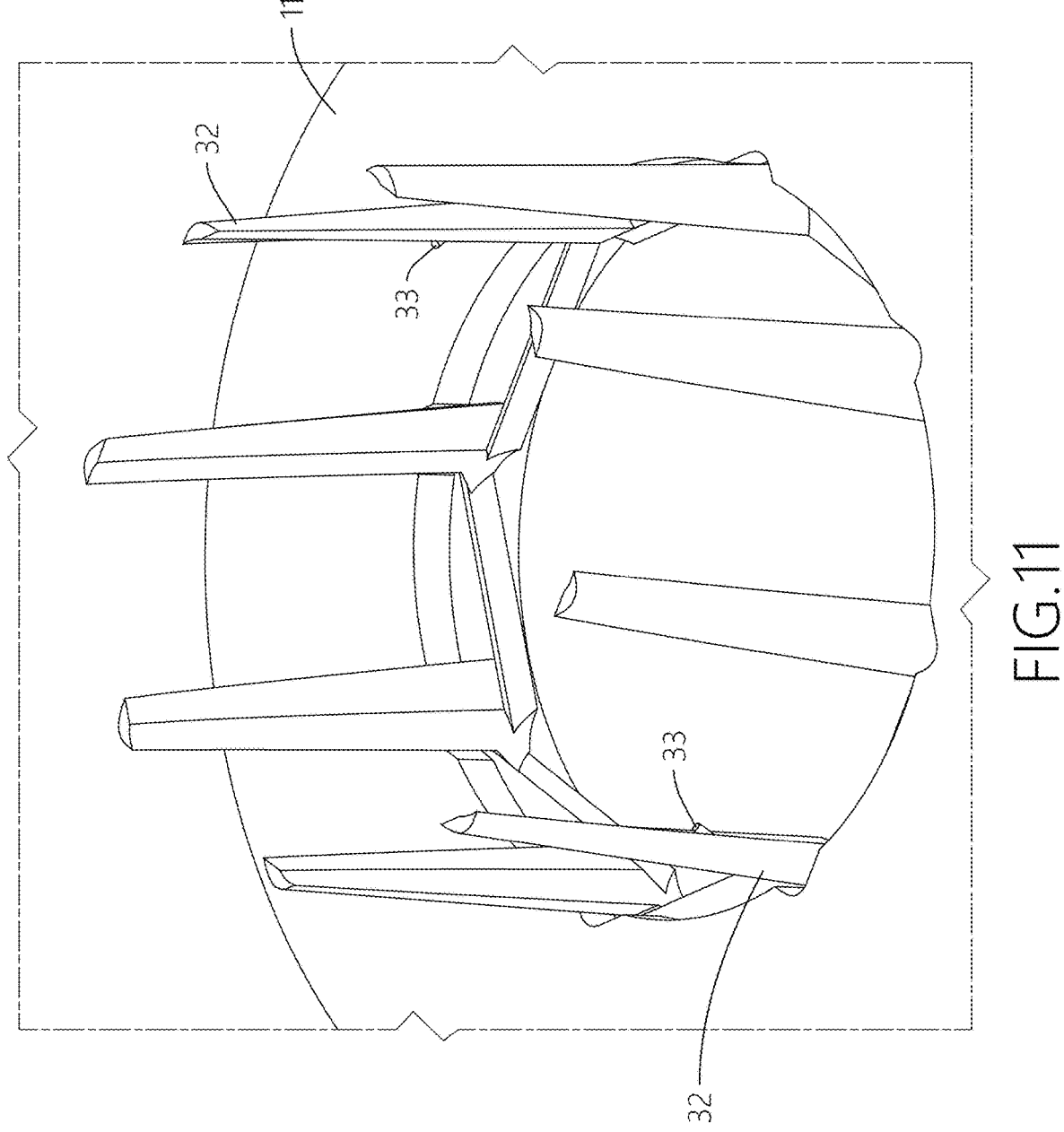
FIG. 11 is an enlarged perspective view of the annular surgical retractor in FIG. 1, shown in the expanding state.
Figure 12:
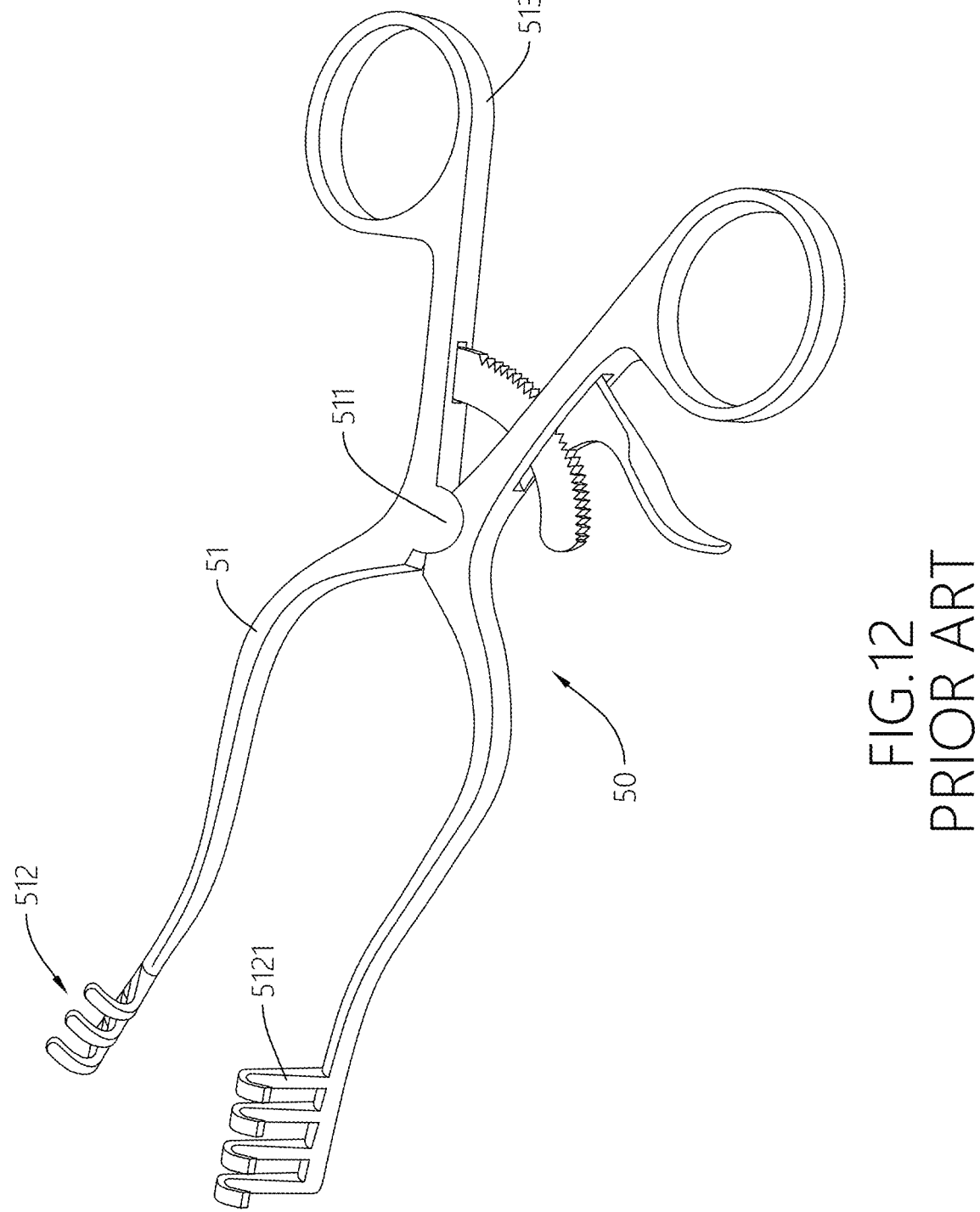
FIG. 12 is a perspective view of a conventional surgical retractor in accordance with the prior art.
Figure 13:
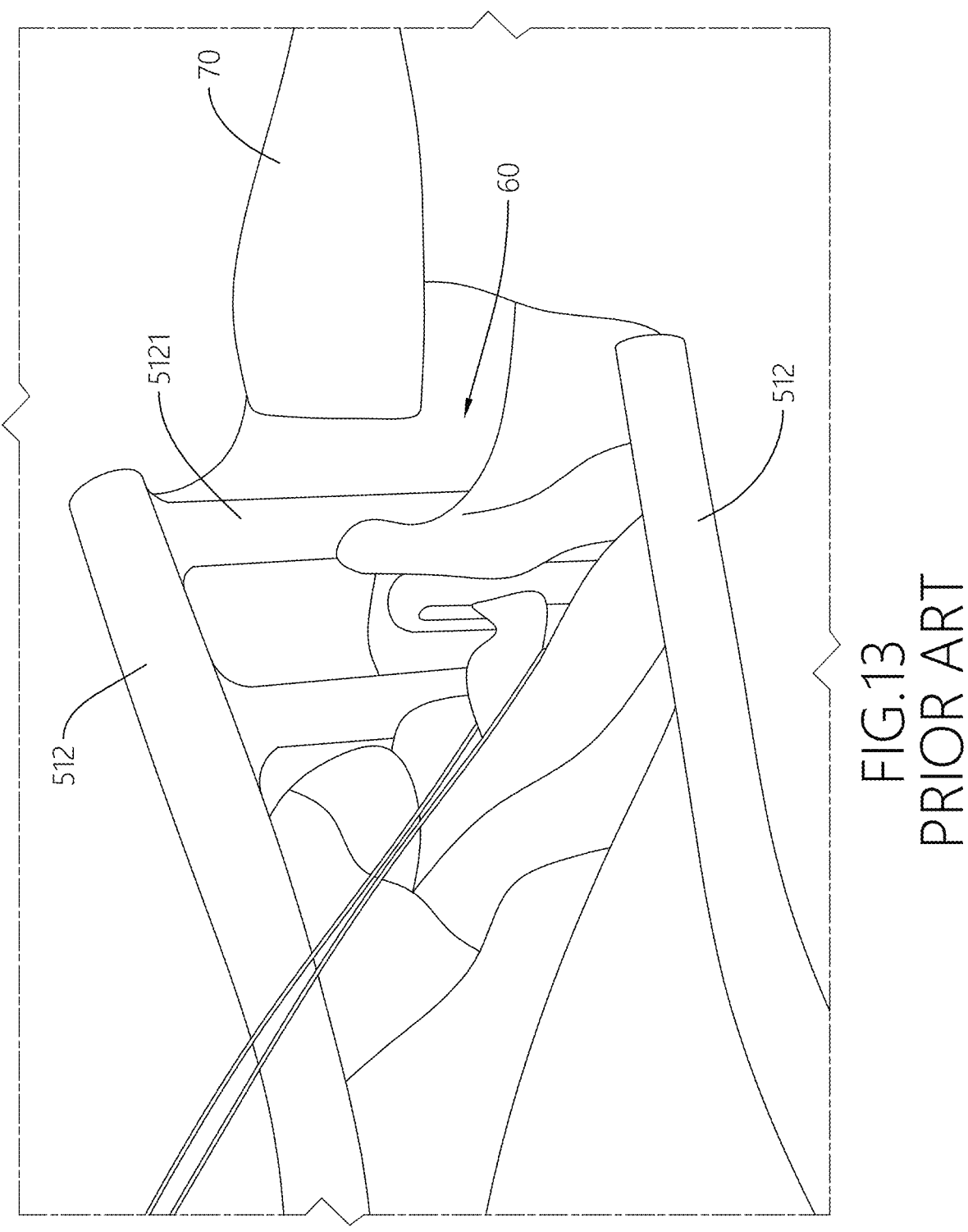
FIG. 13 is an operational perspective view of the conventional surgical retractor in FIG. 12.

With further reference to FIG. 11, at least one compact camera module 33 may be further mounted on the supporting rod 32 of at least one of the expanding elements 30, so that the at least one camera module 33 is able to be inserted into the incision along with the supporting rods 32 to capture images of internal tissues. The operator is able to observe the internal tissues through monitor, so as to accurately determine how to proceed with the following treatment. When the at least one compact camera module 33 includes a plurality of compact camera modules 33, the compact camera modules 33 are evenly distributed on the supporting rods 32, to photograph or to film different locations of the internal tissues from different angles. In the preferred embodiment as shown in FIG. 11, the at least one compact camera module 33 includes two compact camera modules 33. The two compact camera modules 33 are mounted on two of the supporting rods 32 that are disposed opposite to each other, so as to photograph or to film the internal tissues at different angle as much as possible.

Figure 2:
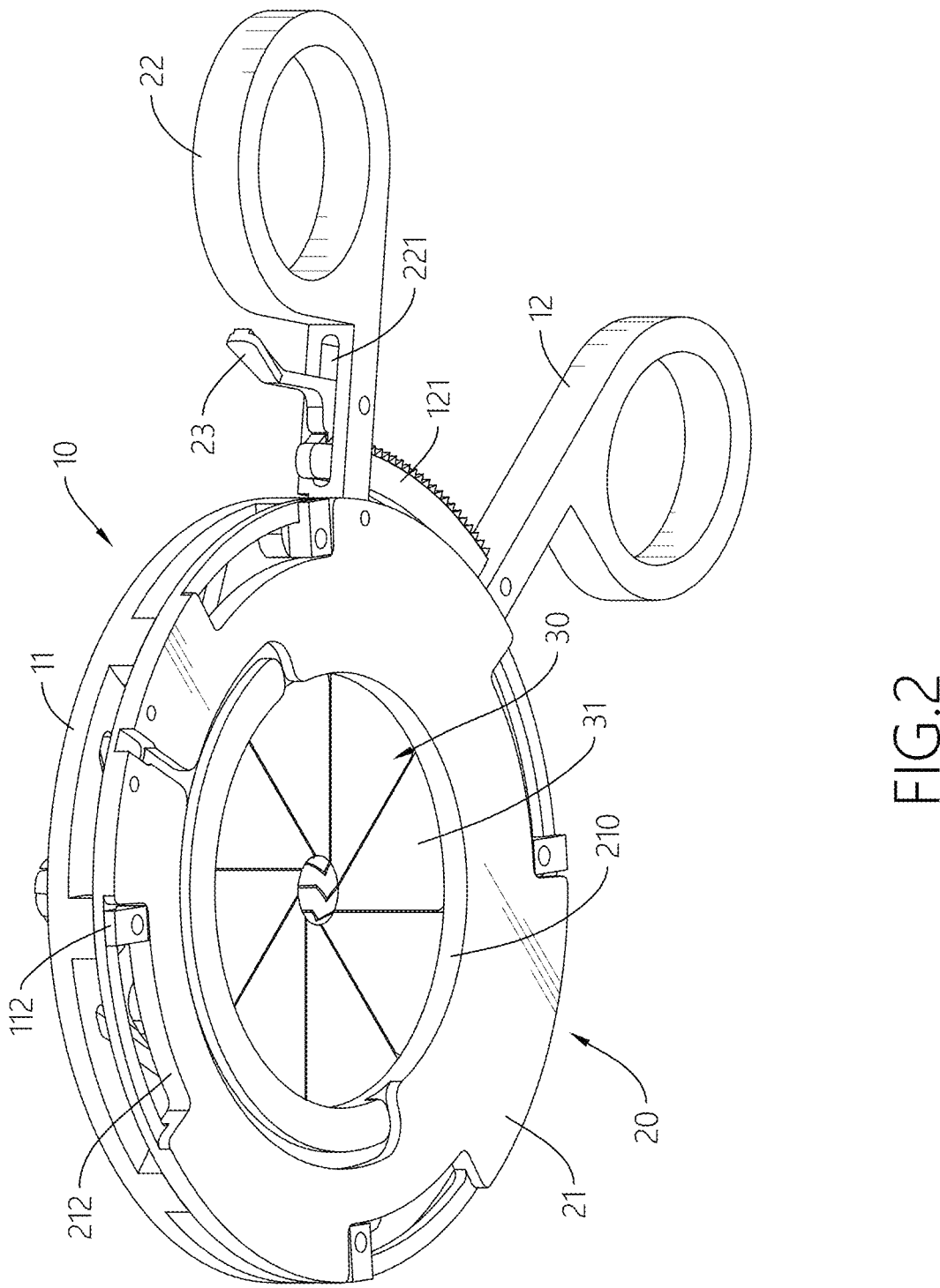
FIG. 2 is a bottom perspective view of the annular surgical retractor in FIG. 1, shown in the retracting state.

With reference to FIGS. 1 and 2, in the preferred embodiment, the movable handle 22 further has a mounting hole 221 formed through the movable handle 22. A positioning element 23 is mounted in the mounting hole 221 and has at least one positioning tooth 231. A curved rack 121 is mounted through the mounting hole 221 of the movable handle 22 and has an end securely connected to the stationary handle 12. The at least one positioning tooth 231 of the positioning element 23 resiliently engages with the curved rack 121. Thus, when the movable annular plate 21 rotates a required angle relative to the stationary annular plate 11, a relative angular position of the movable annular plate 21 and the stationary annular plate 21 can be fixed, and the area surrounded by the supporting rods 32 of the expanding elements 30 is stayed at a proper range.

The annular surgical retractor as described has the following advantages. When using the annular surgical retractor, the incision to be expanded only need to be about 8 millimeter (mm) to allow the supporting rods 32 of the expanding elements 30 to be inserted into the incision. Small incision can reduce a burden on the patient and effectively shorten healing time. Moreover, a depth of the supporting rods 32 inserted into the incision and the area surrounded by the supporting rods 32 can be adjusted according to the surgical needs. The maximum depth of the supporting rods 32 inserted into the incision may be 30.8 mm. In addition, when the supporting rods 32 of the expanding elements 30 move toward the expanding positions, the area for performing surgery surrounded by the supporting rods 32 is annular expanded. That is, the operator is able to push the internal tissues in all directions around at the same time, making the annular surgical retractor highly flexible in use. The elastic sleeve 40 further prevents the internal tissues from invading the area for surgery, which effectively improving safety of the surgery.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An annular surgical retractor comprising:
   a base panel including
   a stationary annular plate having
   a through hole formed through the stationary annular plate; and
   multiple guiding portions disposed on an inner side surface of the stationary annular plate and sequentially arranged around the through hole of the stationary annular plate; each of the guiding portions being elongated and having a retracting end positioned toward an inner annular edge of the stationary annular plate and an expanding end positioned toward an outer annular edge of the stationary annular plate; the retracting end of the guiding portion and the expanding end of the guiding portion located at different radial extension lines of the stationary annular plate; and
   a stationary handle securely attached to the outer annular edge of the stationary annular plate;
   a driving panel including
   a movable annular plate having
   a through hole formed through the movable annular plate;
   an inner side surface facing toward the inner side surface of the stationary annular plate; and
   multiple driving portions disposed on the inner side surface of the movable annular plate and arranged around the through hole of the movable annular plate; and
   a movable handle securely attached to an outer annular edge of the movable annular plate; and
   multiple expanding elements disposed between the base panel and the driving panel and arranged annularly, each of the expanding elements having
   a transmission panel disposed between the stationary annular plate and the movable annular plate, and having
   a first side surface facing toward the stationary annular plate;
   a second side surface facing toward the movable annular plate;
   an inner end disposed between the through hole of the stationary annular plate and the through hole of the movable annular plate;
   an outer end disposed between the stationary annular plate and the movable annular plate;
   a sliding portion disposed on the first side surface of the transmission panel, wherein the sliding portions of the transmission panels of the expanding elements are movably mounted with the guiding portions of the stationary annular plates to allow each of the sliding portions to move along a respective one of the guiding portions; and
   a transmission portion disposed on the second side surface of the transmission panel, the transmission portion having a retracting end positioned toward the outer annular edge of the movable annular plate and an expanding end positioned toward an inner annular edge of the movable annular plate, wherein the transmission portions of the transmission panels of the expanding elements are movably mounted with the driving portions of the movable annular plate to allow each of the driving portions to move along a respective one of the transmission portions; and
   a supporting rod formed on the inner end of the transmission panel, being bent relative to the transmission panel, and protruding outward from the through hole of the stationary annular plate;
   wherein the expanding elements are driven by the driving panel to move back and forth between a retracting position and an expanding position;
   wherein when each of the expanding elements is located at the retracting position, each of the driving portions of the movable annular plate is located at the retracting end of the transmission portion of a respective one of the expanding elements, the sliding portion of each of the expanding elements is located at the retracting end of a respective one of the guiding portions of the stationary annular plate, and the supporting rods of the expanding elements abut on each other side by side to form a column;

wherein when each of the expanding elements is moved to the expanding position, each of the driving portions of the movable annular plate is moved to the expanding end of the transmission portion of a respective one of the expanding elements, the sliding portion of each of the expanding elements is moved to the expanding end of the respective one the guiding portions of the stationary annular plate, and the supporting rods of the expanding elements are separately arranged annularly.

2. The annular surgical retractor as claimed in claim 1, further comprising at least one compact camera module mounted on the supporting rod of at least one of the expanding elements.

3. The annular surgical retractor as claimed in claim 2, wherein the at least one compact camera module includes two compact camera modules mounted on two of the supporting rods that are disposed opposite to each other.

4. The annular surgical retractor as claimed in claim 2, further comprising an elastic sleeve mounted around the supporting rods of the expanding elements.

5. The annular surgical retractor as claimed in claim 2, wherein an included angle between the supporting rod and the transmission panel is defined between 90 degrees to 100 degrees.

6. The annular surgical retractor as claimed in claim 1, further comprising an elastic sleeve mounted around the supporting rods of the expanding elements.

7. The annular surgical retractor as claimed in claim 6, wherein an included angle between the supporting rod and the transmission panel is defined between 90 degrees to 100 degrees.

8. The annular surgical retractor as claimed in claim 1, wherein an included angle between the supporting rod and the transmission panel is defined between 90 degrees to 100 degrees.

9. The annular surgical retractor as claimed in claim 1, wherein the movable annular plate of the driving panel further has multiple limiting guide slots separately arranged along the outer annular edge of the movable annular plate, each of the limiting guide slots formed as an arc-shaped elongated hole and extending along the outer annular edge of the movable annular plate; and the stationary annular plate of the base panel further has multiple limiting protrusions disposed on the inner side surface of the stationary annular plate, separately arranged along the outer annular edge of the stationary annular plate, and slidably protrude in the limiting guide slots 212 respectively.

10. The annular surgical retractor as claimed in claim 9, wherein the limiting protrusions are detachably mounted on the inner side surface of the stationary annular plate.

11. The annular surgical retractor as claimed in claim 1, wherein each of the guiding portions of the stationary annular plate is formed as an elongated guiding groove; and the sliding portion of each of the expanding elements is formed as a protrusion and is mounted in the respective one of the guiding portions.

12. The annular surgical retractor as claimed in claim 11, wherein the sliding portion of each of the expanding elements is formed into an elongated protrusion with a length shorter than the guiding portion.

13. The annular surgical retractor as claimed in claim 11, wherein the transmission portion of the transmission panel of each of the expanding elements is formed as an elongated guiding groove; and each of the driving portions of the movable annular plate is formed as a protrusion and is mounted in the respective one of the transmission portions.

14. The annular surgical retractor as claimed in claim 1, wherein the transmission portion of the transmission panel of each of the expanding elements is formed as an elongated guiding groove; and each of the driving portions of the movable annular plate is formed as a protrusion and is mounted in the respective one of the transmission portions.

15. The annular surgical retractor as claimed in claim 1, wherein the movable handle further has a mounting hole formed through the movable handle;

a positioning element is mounted in the mounting hole and has at least one positioning tooth;

a curved rack is mounted through the mounting hole of the movable handle and has an end securely connected to the stationary handle;

wherein the at least one positioning tooth of the positioning element resiliently engages with the curved rack.

* * * * *